United States Patent [19]

McKenna

[11] Patent Number: 4,478,763

[45] Date of Patent: Oct. 23, 1984

[54] PROCESS FOR PREPARING ALPHA-FLUORINATED ALKANEDIPHOSPHONATES

[75] Inventor: Charles E. McKenna, Los Angeles, Calif.

[73] Assignee: Univ. of Southern California, Los Angeles, Calif.

[21] Appl. No.: 435,578

[22] Filed: Oct. 20, 1982

[51] Int. Cl.$^3$ ............................. C07F 9/40; C07F 9/38
[52] U.S. Cl. ..................................... 260/986; 260/932; 260/502.4 P
[58] Field of Search ......................................... 260/986

[56] References Cited

U.S. PATENT DOCUMENTS 4,330,486  5/1982  Burton et al. ........................ 260/932

OTHER PUBLICATIONS

McKenna et al., "J. Org. Chem.", vol. 46, pp. 4573–4576, 10/27/1981.
Burton, et al., "J. Fluorine Chem.", vol. 20, pp. 617–626, (1982).
Kosolapoff et al., "Org. Phosphorus Cpds.", vol. 7, p. 181 (1977).
Abstracts Relating to British Patent No.1,026,366; issued Apr. 20, 1966.
Burton, et al., "Preparation of F-Methylene Bis Phosphonates", *Journal of Fluorine Chemistry*, 15 (1980) pp. 263–266.
Blackburn, et al., "Monofluoro- and Difluoro-methylenebisphosphonic Acids: Isopolar Analogues of Pyrophosphoric Acid", *J.C.S. Chem. Comm.*, 1981, pp. 930–932.

*Primary Examiner*—Anton H. Sutto
*Attorney, Agent, or Firm*—Nilsson, Robbins, Dalgarn, Berliner, Carson & Wurst

[57] ABSTRACT

A method for the production of alpha-fluorinated methane diphosphonates consists of the reaction of diphosphonate esters with a strong base, preferably potassium t-butoxide, and perchloryl fluoride to produce alpha-mono and alpha,alpha-difluorinated derivatives which can be converted to the corresponding acids by mild hydrolysis. The synthesis of unsymmetrical alpha-fluorinated methanediphosphonate esters followed by selective hydrolysis produces unsymmetrical diesters of diphosphonic acids.

4 Claims, No Drawings

PROCESS FOR PREPARING ALPHA-FLUORINATED ALKANEDIPHOSPHONATES

FIELD OF THE INVENTION

This invention relates to the general field of phosphorous chemistry, and is particularly concerned with a method for the production of alpha-fluorinated methane diphosphonates.

BACKGROUND AND SUMMARY OF THE INVENTION

Phosphonates are derivatives of the hypothetical phosphonic acid, $HP(O)(OH)_2$, and have been widely investigated as models for phosphate esters because they have an approximately isoteric relationship and because the C-C-P linkage is more resistant to hydrolysis than is the C-O-P linkage. Monofluoro and difluoro methanediphosphonic acids are useful as carbon analogs of pyrophosphoric acid in that the fluorinated methane group is equal to the central oxygen atom of pyrophosphoric acid, but the P-C-P bonds cannot be easily broken by enzymes or other means.

As pyrophosphate analogs, fluorinated methanediphosphonic acids are useful in biological and medical applications with respect to bone disorders and other circumstances involving pyrophosphate metabolism. The alpha fluorination of the diphosphonic esters heightens their similarity to the corresponding phosphoric acid esters. This is due to the fact that the fluorinated alpha-$CH_2$ group has an electro-negativity which is similar to that of oxygen in the phosphoric acid compounds. Specific examples of useful biological-medical applications include the treatment of Paget's disease and osteoporosis of bone, the bone-specific delivery of chelated radioactive metal ions and drug-active moieties.

While the direct halogenation of tetra-alkyl methanediphosphonates is a proven method for the preparation of mono and dichloro, bromo and iodo derivatives, methods for the direct fluorination of such esters have shown poor results. The use of fluorine gas, perfluoropiperidine or perfluoro 2,6-dimethylpiperidine have each led to partial fluorine substitution for hydrogen at all possible sites in tetraethyl methanediphosphonate. Tetraethyl difluoro methanediphosphonate has been prepared with a 12% overall yield from dibromo difluoromethane and sodium diethylphosphonate via diethyl bromodifluoro methanephosphonate.

According to the present invention, a direct method to fluorinated alkanediphosphanates is provided by the reaction of alkanediphosphonate esters with perchloryl fluoride. Perchloryl fluoride reacts smoothly with tetraalkyl or tetraaromatic lower alkanediphosphonate carbanions to form the corresponding fluorophosphonate esters. The diphosphonate carbanion is produced by a strong base such as sodium, sodium hydride or sodium ethoxide, but if potassium tert-butoxide is used as a base, the total yield of fluorinated phosphonate esters approaches 85%.

The fluorination reaction proceeds virtually as a titration of base with perchloryl fluoride and shows a readily recognizable end point marked by a characteristic color change from dark to pale yellow. Termination of the reaction is also indicated by the end of a temperature rise accompanying the reaction and cessation of perchloryl fluoride uptake.

Hydrolysis of the monofluoro and difluoro diphosphonate esters yields the respective fluoro alkanediphosphonic acid and difluoro alkanediphosphonic acid. As an example, when compared with the parent methanediphosphonic acid, these new compounds show a smooth trend of decreasing melting point and increased nuclear magnetic shielding at phosphorous as the alpha hydrogen atoms of methanediphosphonic acid are replaced by fluorine atoms relative to $H_3PO_4$.

The methanediphosphonate ester is first reacted with the base to form a carbanion $$[(RO)_2P(O)]_2CH^- \qquad (I)$$

which reacts with $FClO_3$ to form the monofluoro ester $$[(RO)_2P(O)]_2CFH \qquad (II)$$

Further treatment with the base yields a second carbanion $$[(RO)_2P(O)]_2CF^- \qquad (III)$$

which reacts similarly upon exposure to $FClO_3$ to form the difluoro ester $$[(RO)_2P(O)]_2CF_2 \qquad (IV)$$

Hydrolysis of the methanediphosphonic esters to the corresponding diphosphonic acids may be accomplished by any one of a number of methods known in the art. A preferred method is the treatment of the esters II and IV with bromotrimethylsilane to produce the trimethylsilyl esters $$[(TMSO)_2P(O)]_2CFH \qquad (V)$$

and $$[(TMSO)_2P(O)]_2CF_2 \qquad (VI)$$

respectively.

Hydrolysis of the esters V and VI affords, respectively, fluoro methanediphosphonic acid $$[(HO)_2P(O)]_2CFH \qquad (VII)$$

and difluoro methanediphosphonic acid $$[(HO)_2P(O)]_2CF_2 \qquad (VIII)$$

In the above formulas, R may be any alkyl or aromatic group and the choice of the group R has been shown to have no effect upon the fluorination reactions of the present invention. Thus, R may be methyl, ethyl, propyl, butyl, benzyl, phenyl or a higher group as desired.

In another aspect of the invention, unsymmetrical fluorinated methanediphosphonate esters are synthesized and selectively hydrolized to form unsymmetrical diphosphonic acids i.e., half-acids. In a reaction similar to that described above, unsymmetrical unfluorinated ester carbanions having the formula

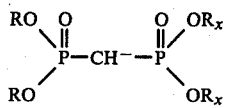
(IX)

react with $FClO_3$ to form $$(RO)_2P(O)-CFH-P(O)(OR_x)_2 \quad (X)$$

and, alternatively, react further to form $$(RO)_2P(O)-CF_2-P(O)(OR_x)_2 \quad (XI)$$

R and $R_x$, while dissimilar, may be any alkyl or aromatic group, although methyl, ethyl, propyl, butyl, benzyl or phenyl may be preferred as more complex groups offer no advantage with respect to the basic fluorination reaction.

Treatment with bromotrimethylsilane, as described, or other selective hydrolysis of the esters X and XI, respectively, yields the unsymmetrical half-esters

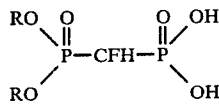

(XII)

and

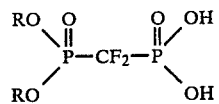

(XIII)

With regard to the formation of the half-esters XII and XIII, R and $R_x$ are selected on the basis that the group having the smaller steric bulk will be converted first to the acid i.e., when R is isopropyl and $R_x$ is methyl, the reaction of $R_x$ proceeds first to produce bis-diisopropyl mono- or difluoro methanediphosphonic acid. Similarly, the silyldealkylation and hydrolysis reaction prefers primary carbon groups over secondary over tertiary, so that propyl groups will convert before isopropyl and isopropyl in turn, before t-butyl. The preferred $R_x$ is methyl due to its low steric bulk and primary form.

Other methods of selective hydrolysis may reverse the above described preference and convert the larger group to the acid before the smaller. R, $R_x$ and the hydrolysis method may each be selected as circumstances suggest or render expedient.

DETAILED DESCRIPTION

The method of the present invention for the preparation of alpha-fluorinated methanediphosphonates comprises the process of reacting a methanediphosphonate ester having the formula

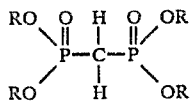

(XIV)

with perchloryl fluoride in the presence of a base, where R is an alkyl or aromatic radical.

EXAMPLE 1

Synthesis of Tetraethyl Fluoro Methanediphosphonate

A solution of tetraethyl methanediphosphonate (12.3 g, 0.043 mol) in dry toluene (10 ml) was added dropwise under a nitrogen atmosphere to a well-stirred partial solution of potassium tert-butoxide (9.60 g, 0.086 mol) in the same solvent (80 ml) cooled externally with ice to 5° C. Perchloryl fluoride was passed rapidly into the vigorously stirred mixture by a subsurface addition tube, producing a noticeably exothermic reaction. The temperature was maintained below 22° C. When neutralization was evident, after a period of 50 minutes and indicated as hereinbefore described, the turbid reaction mixture was suction filtered. A precipitate was washed with several portions of ether and the combined filtrate evaporated (10 mm, 50° C.) to leave a mixture (11.6 g) comprising 34% tetraethyl fluoro methanediphosphonate, 21% tetraethyl difluoro methanediphosphonate and 7% of a monophosphoryl side product having the formula $$(EtO)_2P(O)-CF_2H \quad (XV)$$

The monofluoro and difluoro compounds could not be easily separated by fractional distillation due to their similar boiling points. However, they were readily separated by flash chromatography on a 41 mm by 460 mm column of 40-63-nm silica gel 60 with ethyl acetate/ethanol (9:1) to yield four fractions, I–IV. Fraction IV (6%) was recovered starting material and Fraction II was a mixture which on further chromatography was resolved into I and III. Fraction III, identified as tetraethyl fluoro methanediphosphonate, was vacuum distilled to give an analytical sample: colorless oil; boiling point 112°–115° C. (0.02 mm); TLC (EtOAc)$R_f$0.31; IR (neat) 1255 cm$^{-1}$ (s, phosphoryl); $^1$H NMR (CDCl$_3$) $\delta$1.38 (t,J=7 Hz, 4CH$_3$), 4.30 (m,4OCH$_2$),5.00 (dt,$J_{HF}$=44 Hz,$J_{HP}$=14 Hz,CHF); $^{19}$F NMR (neat) $\delta$222.9(dt,$J_{FP}$=61 Hz,$J_{FH}$=44 Hz); $^{31}$P NMR (neat) $\delta$12.3 (ddp,$J_{PF}$=62 Hz, $J_{PH}$=14 Hz, $J_{PH}$=4 Hz).

Analysis calculated for C$_9$H$_{21}$O$_6$FP$_2$; C,35.30, H,6.91. Found: C, 34.93, H, 7.32.

Fraction I, identified as tetraethyl difluoro methanediphosphonate was vacuum distilled to give an analytical sample: colorless oil; bp 98°–99° C. (0.01 mm)[lit.$^4$bp 115°–118° C. (0.4 mm)]; TLC(EtOAc)$R_f$0.53; IR (neat) 1270 cm$^{-1}$ (s,phosphoryl); $^1$H NMR (CDCl$_3$) $\delta$1.40 (t,J=7 Hz,4CH$_3$), 4.35 (m,4OCH$_2$) (lit.$^4$ $\delta$1.40, 4.39); $^{19}$F NMR (CDCl$_3$) $\delta$120.6 (t,$J_{FP}$=86 Hz) (lit.$^4$, $\delta$122); $^{31}$P NMR (CDCl$_3$) $\delta$4.3 (tp,$J_{PF}$=86 Hz, $J_{PH}$=4 Hz)(lit.$^4$, $\delta$3.4).

The diethyl difluoro methanephosphonate side product, from Fraction I, produced the following properties: $^1$H NMR $\delta$1.38 (t,J=7 Hz, 2CH$_3$), 4.3 (m, 2OCH$_2$), 5.97 (dt, $J_{HP}$=26 Hz,$J_{HF}$=48 Hz, F$_2$CH); $^{19}$F NMR $\delta$133.8 (dd,$J_{FP}$=90 Hz,$J_{FH}$=46 Hz)(lit.$^4$, $\delta$136); $^{31}$P NMR $\delta$4.1 (t,$J_{PF}$=91 Hz).

EXAMPLE 2

Preparation of Tetraisopropyl Fluoro Methanediphosphonate

By use of the same procedure, tetraisopropyl methanediphosphonate (11.8 g, 0.0342 mol) was reacted with potassium tert-butoxide (7.67 g, 0.0684 mol) and toluene (70 ml) followed by perchloryl fluoride to yield 4.56 g (42%) of tetraisopropyl fluoro methanediphosphonate and 5.56 g (43%) of tetraisopropyl difluoro methanediphosphonate. Only a trace of diisopropyl difluoro methanephosphonate was detectable by $^{19}$F NMR. Further treatment of the isolated product mixture (3.71 g, 0.01 mol) with potassium tert-butoxide (0.75 g, 0.0067 mol) and perchloryl fluoride gave 2.78 g (73%) of tetraisopropyl difluoro methanediphosphonate and 0.29 g (8%) of recovered monofluorinated ester. When equimolar amounts of tetraisopropyl methane diphosphonate (8.59 g, 0.025 mol) and potassium tert-butoxide (2.80 g, 0.025 mol) were combined similarly and treated with one equivalent of perchloryl fluoride, 4.45 g (48%) of tetraisopropyl fluoro methanediphosphonate was obtained with 1.3 g (13%) of the difluorinated ester.

The tetraisopropyl fluoro methanediphosphonate was a colorless oil: bp 101°–103° C. (0.02 mm); TLC(EtOAc/benzene, 2:1) $R_f$0.33; IR (neat) 1258 cm$^{-1}$ (s,phosphoryl); $^1$H NMR $\delta$1.26 (d,J=6 Hz, 8CH$_3$), 4.77 (m,OCH), 4.82 (dt, $J_{HP}$=14 Hz,$J_{HF}$=44 Hz,CFH); $^{19}$F NMR (neat) $\delta$221 (dt,$J_{FP}$=63 Hz,$J_{FH}$=44 Hz); $^{31}$P NMR (neat) $\delta$10.7 (ddt,$J_{PF}$=63 Hz, $J_{PH}$=12 Hz, $J_{PH}$=3 Hz).

Analysis calculated for C$_{13}$H$_{29}$O$_6$FP$_2$: C, 43.09; H, 8.07. Found: C, 42.96; H, 8.37.

The tetraisopropyl difluoro methanediphosphonate was isolated as a colorless oil: bp 97°–100° C. (0.01 mm); TLC (EtOAc/benzene, 2:1) $R_f$ 0.55; IR (neat) 1270 cm$^{-1}$ (s,phosphoryl); $^1$H NMR (CDCl$_3$) $\delta$1.40 (d, J=6 Hz, 8CH$_3$), 4.93 (m,4OCH); $^{19}$F NMR (neat) $\delta$121 (t,$J_{FP}$=85 Hz); $^{31}$P NMR (neat) $\delta$2.80 (tt,$J_{PF}$=84 Hz, $J_{PH}$=3 Hz).

Analysis calculated for C$_{13}$H$_{28}$O$_6$F$_2$P$_2$: C, 41.05; H, 7.42. Found: C, 40.82; H, 7.67.

EXAMPLE 3

Preparation of Tetrakis (trimethylsilyl) Fluoro Methanediphosphonate

Bromotrimethylsilane (15.3 g, 0.100 mol) was added dropwise with stirring to 6.15 g (0.0200 mol) of tetraethyl fluoro methanediphosphonate produced in accordance with Example 1. After 3 hours at room temperature and an additional 3 hours at 50° C., ethyl bromide and excess silylating reagent were removed by rotary evaporation at reduced pressure to leave 9.65 g (100%) of the crude product, which was distilled to give 6.95 g (72%) of a pure compound having the formula [(TMSO)$_2$P(O)]$_2$CFH: colorless oil; bp 99°–100° C. (0.01 mm); $^1$H NMR $\delta$0.35 (s, 12CH$_3$), 4.74 (dt, $J_{HF}$=47 Hz, $J_{HP}$=14 Hz, FCH); $^{19}$F NMR $\delta$218 (dt,$J_{FH}$=46 Hz, $J_{FP}$=68 Hz); $^{31}$P NMR $\delta$−7.3 (d,$J_{PF}$=67 Hz).

Using the same reaction, but with longer heating, the same product was obtained by similar treatment of the tetraisopropyl fluoro methanediphosphonate of Example 2.

EXAMPLE 4

Tetrakis (trimethylsilyl) Difluoromethanediphosphonate

Bromotrimethylsilane (7.7 g, 0.050 mol) was stirred with tetraethyl difluoro methanediphosphonate (3.00 g, 0.0092 mol) at room temperature overnight. Evaporation as described in Example 3 gave 4.52 g (98%) of a compound having the formula [(TMSO)$_2$P(O)]$_2$CF$_2$. Vacuum distillation provided an analytical sample: 3.30 g (72%); bp 93°–95° C. (0.02 mm); $^1$H NMR $\delta$0.37 (s, 12CH$_3$); $^{19}$F NMR $\delta$121 (t,$J_{FP}$=90 Hz); $^{31}$P NMR $\delta$−15.0 (t,$J_{PF}$=90 Hz).

The same product was obtained on similar treatment of tetraisopropyl difluoro methanediphosphonate under more vigorous conditions (10 hours at 70° C.).

EXAMPLE 5

Preparation of Fluoro Methanediphosphonic Acid

To 5.5 g (0.011 mol) of tetrakis trimethylsilyl) fluoro methanediphosphonate, in a 50 ml round-bottomed flask flushed with nitrogen, was added 20 ml of water with stirring. After 30 minutes, the organic phase was separated, and the aqueous phase was extracted twice with 15 ml portions of Et$_2$O and then evaporated to dryness. Further drying over P$_2$O$_5$ at 0.001 mm gave 2.04 g (96%) of the pure acid having the formula

[(HO)$_2$P(O)]$_2$CFH    (XVI)

as a deliquescent, waxy white solid: mp 162°–163° C.; $^{19}$F NMR $\delta$225 (dt,$J_{FH}$=46 Hz, $J_{FP}$=63 Hz); $^{31}$P NMR $\delta$10.5 (d,$J_{PF}$=64 Hz); neutralization equivalent 195 (calculated for CH$_5$O$_6$FP$_2$194).

Analysis calculated for C$_{37}$H$_{74}$O$_6$FN$_3$P$_2$: C, 60.22; H, 10.11; N, 5.69. Found: C, 60.09; H, 10.06; N, 5.66.

EXAMPLE 6

Preparation of Difluoro Methanediphosphonic Acid

By use of the procedure described in Example 5, 2.85 g (0.0057 mol) of tetrakis (trimethylsilyl) difluoro methanediphosphonate was hydrolized with 15 ml of water to yield 1.20 g (99%) of difluoro methanediphosphonic acid as a viscous liquid which solidified on prolonged drying (0.01 mm, over P$_2$O$_5$): mp 87°–90° C.; $^1$H NMR (no resonances in D$_2$O); $^{19}$F NMR $\delta$121 (t,$J_{FP}$=86 Hz); $^{31}$P NMR $\delta$3.7 (t,$J_{PF}$=86 Hz); neutralization equivalent 214 (calcd for CH$_4$O$_6$F$_2$P$_2$212).

Analysis calculated for C$_{37}$H$_{73}$O$_6$F$_2$N$_3$P$_2$: C, 58.79; H, 9.73; N, 5.56. Found: C, 58.55; H, 9.52; N, 5.47.

EXAMPLE 7

Synthesis of O,O-Diisopropyl O',O' Dimethyl Mono- and Difluoro Methanediphosphonate and Derivatives A well-stirred partial solution of 28.6 g (0.26 mol) potassium tert-butoxide in 500 ml toluene was cooled to 5° C. in an ice bath. Temperature was maintained at 5° C. while a solution of 58.8 g (0.20 mol) diisopropyl dimethylmethane diphosphonate in 150 ml toluene was added to the reaction vessel over a 35 minutes period. Perchloryl fluoride was doubled through the reaction mixture for 90 minutes, while the reaction flask was kept at 15° C. with the ice bath. When the reaction was completed, the reaction mixture was neutralized with 300 ml of saturated sodium bicarbonate solution, which was then extracted with 2×600 ml chloroform. The organic layers were combined, dried over magnesium sulfate, filtered and evaporated. The product was a golden oil, which contained 30.3 g (49%) diisopropyl fluoro methanediphosphonate and 16.0 g (24%) diisopropyl dimethyldifluoro methanediphosphonate. The relative yields may be adjusted to favor formation of the difluoro product, by using two or more equivalents of the base. The esters are purified by column chromatography, or by extraction in 2CHCl$_3$-H$_2$O, and can be distilled in vacuo. Treatment of either ester with two equivalents of bromotrimethylsilane, added in 5 aliquots over a 30 minutes period at 30°–35° C., gives the unsymmetrical diisopropyl bis (trimethylsilyl) fluoro methanediphosphonate or difluoro methanediphosphonate in quantitative yield. Careful neutral hydrolysis of these esters at room temperature gives the racemic unsymmetrical 0,0-diisopropyl fluoro methanediphosphonic acid or 0,0-diisopropyl difluoro methanediphosphonic acid in high yield (90–100%). The monofluoro acid racemates may be separated, by standard methods, to yield the component enantiomers.

Results illustrating the effects of some of the reaction parameters are summarized in Table I. By suitable adjustment of the proportion of starting materials, either product can be made to predominate. For example, with one equivalent of potassium tert-butoxide as base, the mono fluoro methane derivative of tetraisopropyl methanediphosphonate was prepared with a 48% yield. With two equivalents of this base, the difluoro derivative could be prepared directly with a 43% yield, with an increase to 73% being possible on further reaction of the monofluoro product. The choice of base is important in this respect, since only a single equivalent of sodium could be used, while NaOEt would be expected to give some alkylation side product. In addition to being a stronger base, potassium tert-butoxide offers the advantage of allowing the addition of more than one equivalent of base if desired while avoiding unwanted alkylation of the carbanion and, in fact, gives the best results.

The yields are also lower when sodium/toluene is used in place of potassium tert-butoxide with the isopropyl ester. With potassium tert-butoxide as the base, yields appear to be somewhat higher with the isopropyl ester than with the ethyl ester, an addition of more than one equivalent of base to the latter is accompanied by the formation of a monophosphoryl side product. This compound evidently arises from a cleavage of the C-P bond in the difluoro ester.

The effect of fluorine substitution on the acidity of methanediphosphonic acid is of interest. Using the empirical equations developed by R. G. Grabenstetter et al. *J. Phys. Chem.* 71, 4194 (1967), estimated $pK°$ values for mono and difluoro methanediphosphonic acid were calculated and compared with experimental $pK°$ data for the parent acid. It should be noted that the cited work set forth two alternative Taft equations for $pK°_4$ on giving an optimal fit with bulkier substitution (e.g., $CH_3$) and one to fit data for less sterically hindering substituents (e.g., H). The second equation gives superior agreement with $pK°_4$ values calculated from 31P chemical shift data for the mono and difluoro methane diphosphonic acid, presumably reflecting the small size of the substituted fluoro group.

The data presented in Table II indicate that the monofluoro acid is predicted to have a $pK°_4$ of approximately 10.1, or one order of magnitude below that of the parent acid, while the fourth proton of the difluoro acid is calculated to be 100-fold more acidic than the unfluorinated parent acid. The acidity of the monofluoro acid is comparable to that of dichloro methanediphosphonic acid ($pK°_4=9.8$, $pK°_3=6.1$), which in turn is weaker than the difluoro substituted acid. The difluoro methanediphosphonic acid is the strongest of the halomethanediphosphonic acids.

The enhanced acidity due to the presence of one or two alpha fluoro groups was also apparent in the derivative chemistry of the mono and difluoro acids. Methanediphosphonic acid forms a bis (dicyclohexylamine) salt, but treatment of the mono and difluoro substituted acids with a small excess of base led to the formation of the tris (dicyclohexylamine) derivatives.

Fluorinated methanediphosphonate esters and acids have widespread biochemical application as pyrophosphate analogs, and specifically as F-labelled, hydrolysis-inert pyrophosphate analogs both per se and as synthates for fluorine containing oligophosphonate analogs of compounds such as ATP. For example, optically active fluoro diphosphonate acid and ester enantiomers can be used to prepare the corresponding specific beta, gamma-fluoromethylene analogs of ADP and other nucleotides. Therapeutically, difluoro methanediphosphonic acid inhibits bone resorption at least as effectively as known drugs. In addition, the fluorinated diphosphonate compounds can differentiate tumor tissue from normal tissue, and are thus useful in diagnosis.

Although the foregoing invention has been described in some detail by way of illustration and example in the form of α-fluorinated methanediphosphonates, fluorinated alkanediphosphonates and their production by the fluorination reaction described herein, e.g. ethylene diphosphonates or other lower alkane diphosphonates are within the scope of the invention, and changes in form and the substitution of equivalents are contemplated as circumstances may suggest or render expedient. Although specific terms have been employed herein, they are intended in a descriptive sense and not for purposes of limitation, the scope of the invention being delineated in the following claims.

TABLE I

Fluorination of Methanediphosphonate Esters

| base | ester | base/ester Ratio | % Yield mono-fluoro- | % Yield di-fluoro- | monophosphoryl side product |
|---|---|---|---|---|---|
| Na | ethyl | 1.25:1 | 24 | 17 | — |
| t-BuOK | ethyl | 2:1 | 34 | 21 | 7 |
| t-BuOK | ethyl | 1:1 | 47 | 16 | trace |
| t-BuOK | ethyl | 1:1* | 22 | 45 | 18 |
| Na | isopropyl | 1.30:1 | 28 | 18 | — |
| t-BuOK | isopropyl | 2:1 | 42 | 43 | trace |
| t-BuOK | isopropyl | 3:1 | 32 | 33 | trace |
| t-BuOK | isopropyl | 1:1 | 48 | 13 | trace |
| t-BuOK | isopropyl | 0.60:1* | 8 | 73 | 11 |

*Retreatment of the preceding reaction mixture

TABLE II $pK°$ Values of Methanediphosphonic Acids (MDPA)

| | MDPA | monofluoro MDPA 31P | monofluoro MDPA σ* | difluoro MDPA 31P | difluoro MDPA σ* |
|---|---|---|---|---|---|
| $pK°_4$ | 11.0 | 10.1 | 10.2 | 9.07 | 9.12 |
| $pK°_3$ | 7.4 | 6.62 | 6.82 | 6.08 | 5.89 |
| $pK°_2$ | 3.1 | 2.78 | 2.33 | 2.57 | 1.34 |

What is claimed is:

1. A process for the preparation of α-fluorinated methanediphosphonates comprising reacting a methanediphosphonate ester having the formula

[(RO₂P(O)]-CH₂-[P(O)(R$_x$O)₂]

with potassium tert-butoxide to form a methanediphosphonate carbanion, and reacting said carbanion with perchloryl fluoride, where R and R$_x$ are the same or dissimilar alkyl or aromatic radicals.

2. The process of claim 1 wherein R and R$_x$ are selected from the group consisting of methyl, ethyl, propyl, butyl, benzyl and phenyl.

3. The process of claim 1 or 2 where the product of the perchloryl fluoride reaction is

[(RO)₂P(O)]—CFH—[P(O)(R$_x$O)₂].

4. The process of claim 1 or 2 where the product of the perchloryl fluoride reaction is

[(RO)₂P(O)]—CF₂—[P(O)(R$_x$O)₂].

* * * * *